United States Patent [19]

Zheng

[11] Patent Number: 5,909,527
[45] Date of Patent: Jun. 1, 1999

[54] AUTOMATIC CURRENT SELECTION FOR SINGLE FIBER SPLICING

[75] Inventor: Wenxin Zheng, Solna, Sweden

[73] Assignee: Telefonaktiebolaget LM Ericsson, Stockholm, Sweden

[21] Appl. No.: 09/023,302

[22] Filed: Feb. 13, 1998

[30] Foreign Application Priority Data

Feb. 14, 1997 [SE] Sweden ................................. 9700532

[51] Int. Cl.⁶ .................................................. G02B 6/255
[52] U.S. Cl. ............................................................ 385/96
[58] Field of Search ........................... 385/88–90, 95–96, 385/98–99, 147; 356/73.1; 374/160, 188; 219/57, 121.11, 121.45; 65/407, 152, 501

[56] References Cited

U.S. PATENT DOCUMENTS

| | | | |
|---|---|---|---|
| 4,319,902 | 3/1982 | Hensel | 385/96 |
| 5,218,184 | 6/1993 | Hakoun et al. | 385/96 |
| 5,546,491 | 8/1996 | Loch | 385/99 |
| 5,570,446 | 10/1996 | Zheng | 385/98 |
| 5,638,476 | 6/1997 | Zheng | 385/96 |
| 5,772,327 | 6/1998 | Zheng | 374/160 |
| 5,849,173 | 12/1998 | Chandross et al. | 205/664 |
| 5,850,283 | 12/1998 | Zheng | 356/73.1 |

FOREIGN PATENT DOCUMENTS

| | | |
|---|---|---|
| 2-28605 | 1/1990 | Japan . |
| 2-2129607 | 5/1990 | Japan . |

OTHER PUBLICATIONS

Zheng, W., "Real Time Control of Arc Fusion for Optical Fiber Splicing" Journal of Lightware Technology, vol. 11, No. 4, Apr. 1993.

Kiss, G. et al., "High Yeild Splicing . . . Electronic Condition", National Fiber Operation Engineering Conference, Denver, USA, Sep., 1996.

Katagiri, T. et al., "Direct Core Observation . . . With Dopants", Electronics and Communication s in Japan, Part 2, vol. 71, No. 11, 1988.

Zheng, W. et al., "Erbiu–Doped Fiber Splicing and Splice Loss Estimation", Journal of Lightware Technology, vol. 12, No. 3, Mar. 1994.

*Primary Examiner*—Akm E. Ullah
*Attorney, Agent, or Firm*—Burns, Doane, Swecker & Mathis, L.L.P.

[57] ABSTRACT

For determining an optimal fusion current to be used in welding the ends of two optical fibers to each other the intensity of light emitted from the fibers is measured when heating the fibers by means of currents between welding electrodes. These currents are selected to be significantly lower than the range, in which the optimal fusion current can be expected to be located. From the relation of the measured light intensity values and the different set currents a functional relationship is obtained, which is used for extrapolating to find the current which produces a higher light intensity value, which is the desired one during the actual welding. This is based on the assumption that the light intensity emitted from the fibers is dependent on the current used when heating the fibers in the electric arc between the welding electrodes. An exponential type relation can be used requiring only two parameters to be measured for each splice and thus two different currents for heating the fiber in the arc is sufficient for determining the optimal fusion. Such a determination is easily implemented in automatic splicers having advanced image processing and logic and arithmetic facilities and gives good results for splices made e.g. on different heights above sea level.

25 Claims, 5 Drawing Sheets

FIG. 6

AUTOMATIC CURRENT SELECTION FOR SINGLE FIBER SPLICING

The invention relates to methods and devices for determining an optimal fusion current to be used in splicing single fibers to each other using an electric arc generated between electrodes.

BACKGROUND

In fusion splicing optical fibers using an electric arc generated between electrodes one of the most important parameters to be selected in the best possible way is the electrode current or fusion current passing between the electrodes in the arc. The electrode current must be determined correctly in order to obtain a low loss and high strength of the splice and an accurate estimation of the optical loss in the splice, see the article W. Zheng, "Real time control of arc fusion for optical fiber splicing", IEEE J. of Lightwave Technology, Vol. 11, No. 4, pp. 548–553, April 1993. The fibers obtained from different vendors, fibers manufactured for different purposes such as single-mode or multi-mode fibers, fibers processed using different treatments, such as fibers coated with titanium or carbon, etc., often need different fusion currents. Even for the same type of fiber, the fusion current has to be increased up to 70% when the place where the fusion welding is made varies from 100 m to 5000 m above sea level owing to the difference in the ambient air pressure. Moreover, since after a number of splices the particles evaporated from the silica fibers will gradually be plated on the surface of the electrodes used for the fusion welding, the current should often be readjusted for the changing conditions of the welding electrodes. To find out a suitable fusion current, many different methods have been developed, such as the well-known melt-back method, see G. Kiss, "High yield fusion splicing in the outside plant: using fiber meltback to monitor electrode condition," National Fiber Operation Engineering Conference, Denver, U.S.A., Sept. 1996, methods using barometric sensors, the offset-splicing method, see the Swedish patent No. 9501589-7, "Auto-fusion temperature control with an offset-splicing method for optical fiber splicing", etc.

SUMMARY

It is an object of the invention to provide a method and device for determining an optimal fusion current to be used in welding single fibers to each other, the method and device having a simple structure and being capable of an easy implementation in commercially available splicing devices.

A determination of an optimal fusion current to be made to pass between electrodes for welding the ends of two optical fibers to each other is based on the assumption that the light intensity emitted from the fibers is dependent on the current used in the heating the fibers in an electric arc between the welding electrodes and that an optimal splice between the fibers is obtained when the temperature of the fiber ends during the welding process is equal to a fixed value, which is independent of various ambient conditions such as the height above sea level. The intensity of light emitted from the fibers is measured when the fibers are heated by means of currents between the electrodes which are significantly lower than the range, where the optimal fusion current can be expected to be located. From the relation of the measured light intensity values and the different heating currents a functional relationship is obtained, which is used for extrapolating to find a value of the current intensity which will produce a higher light intensity value equal to the desired one during the actual welding. An exponential type relation can be used requiring only two parameters to be measured for each splice and thus two different currents for heating the fiber in the arc is sufficient for determining the optimal fusion. Such a determination is easily implemented in automatic splicers having advanced image processing and logic and arithmetic facilities.

Using the method described above the fiber ends will not be destroyed as in the melt-back method, the result will be more reliable than that using barometric sensors and the adaption to the actual splicing situation is much easier than in the offset method.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

A complete understanding of the invention and of the above and other features thereof may be gained from a consideration of the following detailed description of non-limiting embodiments presented hereinbelow with reference to the accompanying drawings, in which.

DETAILED DESCRIPTION

1. Basic Concept

Figure 1A:
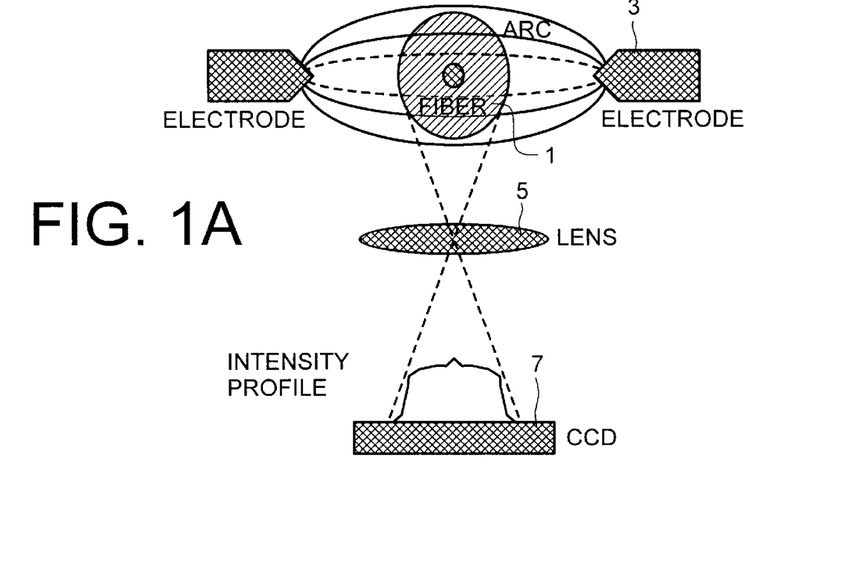
FIG. 1a is schematic picture of the setup in a optical fiber splicer for heating an optical fiber using an electrical discharge and for capturing a light intensity profile of the heated fiber using an optical system.
Figure 6:
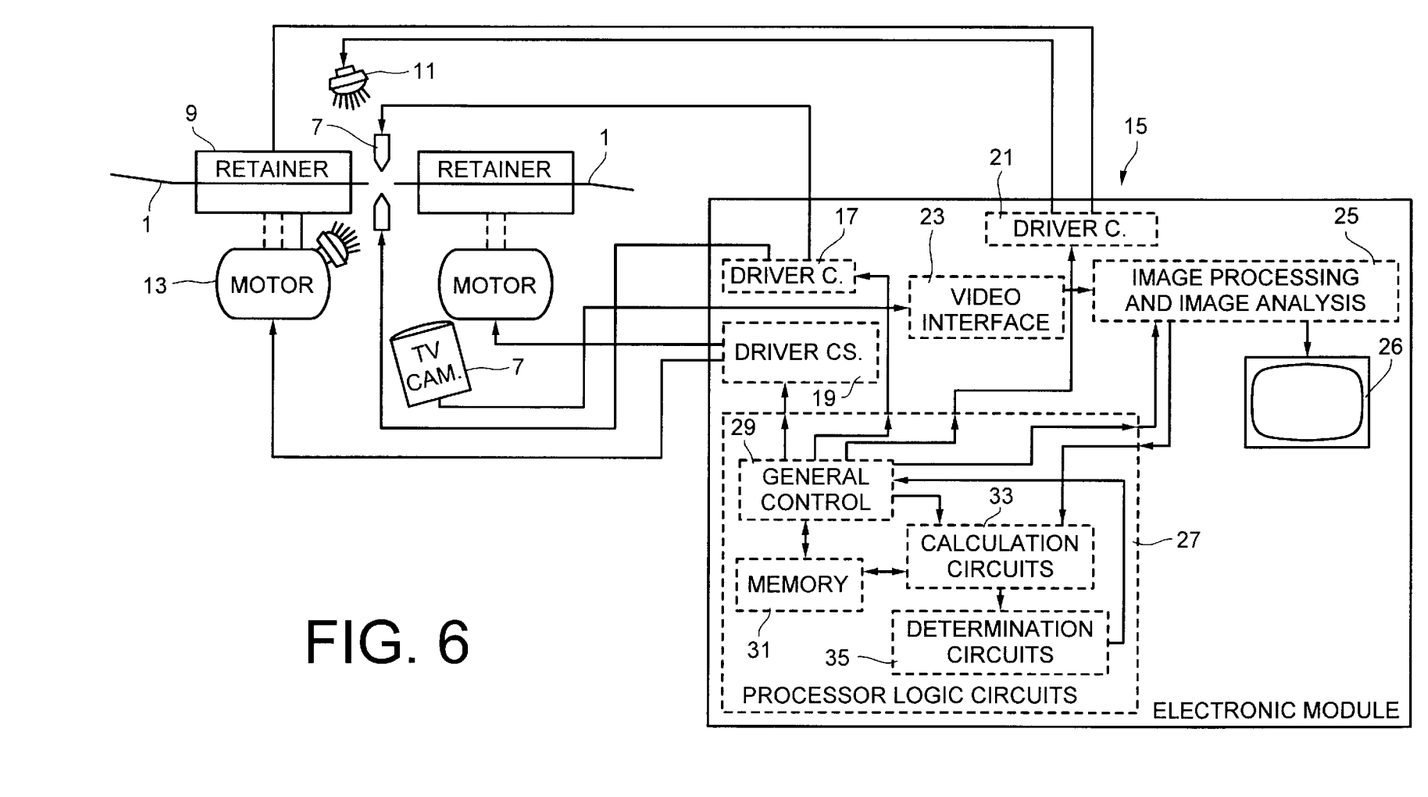
FIG. 6 is a schematic picture illustrating the electric control of an optical fiber splicer.

In FIG. 1a the basic setup in an automatic optical fiber splicer is shown. The optical fiber 1 has its end region located between the points of electrodes 3, between which an electrical glow discharge is generated for heating the fiber end, the intensity of the electrical discharge being controlled by the intensity of the electrical current between the electrodes 3. An optical system symbolized by a lens 5 depicts the fiber end region on the light sensitive area 7 of a camera, e.g. a plate carrying CCD elements. In most automatic fiber fusion splicers of this type digital imaging processing systems, compare FIG. 6, are provided for processing the electric signals from the light sensitive area 7 and thereby for monitoring the fibers used and the splicing procedure by controlling fiber positioning devices, see FIG. 6. The imaging system of such an automatic optical fiber splicer is actually one of the best means for also monitoring the fiber temperature and for controlling the fusion current, as will be apparent from the following description.

Figure 1B:
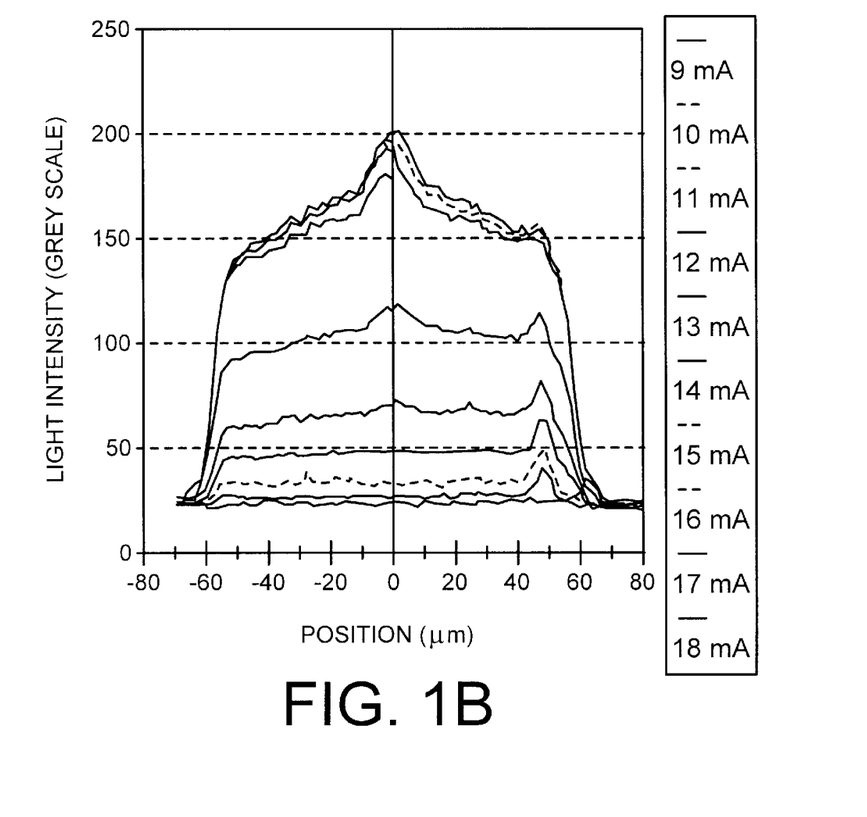
FIG. 1b is a diagram illustrating light intensity profiles of a single mode fiber heated with different fusion currents from 9 to 18 mA.

When an optical fiber is heated, the thermal radiation emitted from the fiber can be observed using a video-camera (symbolized by 7 in FIG. 1a) and analyzed using a digital image processing system of a splicer, as e.g. is described in the paper W. Zheng, O. Hultén and R. Rylander, "Erbium-doped fiber splicing and splice loss estimation", IEEE J. of Lightwave Technology, Vol. 12, No. 3, pp. 430–435, March 1994, which is incorporated by reference herein. During splicing, the radiant emissivity, consequently also the luminescence intensity from the heated fiber, is a function of the temperature at the fiber ends, see the paper T. Katagiri et al., "Direct core observation method using thermal radiation of silica fibers with dopants", Elec. and Comm. in Japan, Vol. 71, No. 11, pp. -85, 1988, and also FIG. 1b, in which a diagram illustrates the light intensity along a line perpendicular to the fiber axis for different fusion currents. Thus, the fiber temperature is a function of the fusion current. The relation between the fusion current and the light intensity can be measured in several different ways, such as peak value detecting, averaging over a part of or over the whole fiber, etc.

Figure 2:
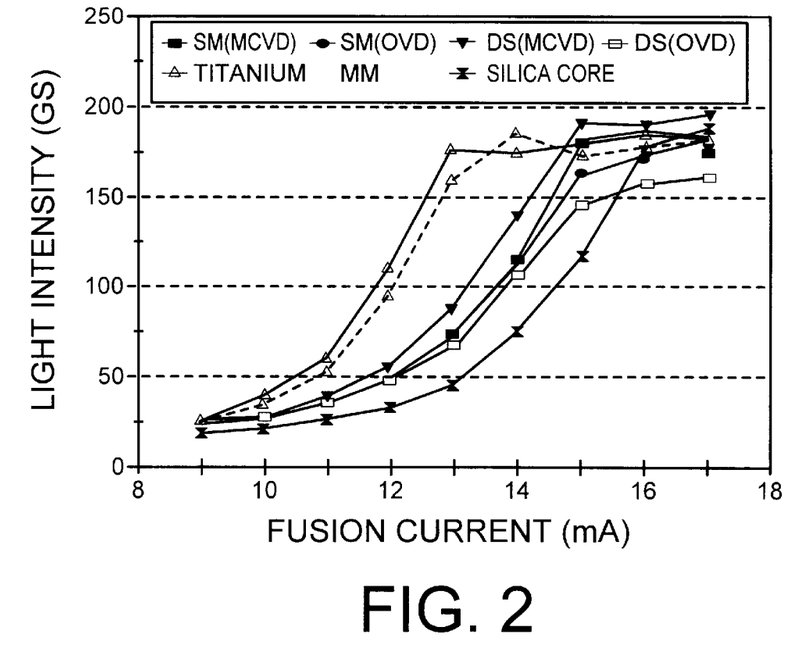
FIG. 2 is a diagram illustrating the fusion current as a function of the luminescence intensity from the fiber ends.

In FIG. 2 the measured average light intensity at the fiber central region taken as having a width about half the fiber diameter is shown as a function of the fusion current, e.g. here also taken along a line perpendicular to the fiber axis, for seven different fiber types. The unit of the abscissa axis is in grey scale units obtained from the camera system. The light intensity values are computed by averaging readings of a perpendicular line having a length of 60 µm at the central part of fiber (from −30 µm to +30 µm, compare FIG. 1b). The abbreviations/designations in the figure mean: SM: single mode fiber; DS: dispersion shifted fiber; Titanium: titanium coated fiber; MM: multi-mode fiber. From the figure, we can clearly observe the Automatic Gain Control (AGC) function of the camera which is activated when the average intensity (not the maximum intensity) of the captured image is higher than 150 grey scales (GS). Normally, if the maximum intensity in one picture is higher than about 200 grey scale units for a 16-bit grey-scale resolution having 255 different grey scale values or units, the AGC function of such a digital camera will be triggered on, and the average intensity in the captured image will be decreased. In this way, such a 16-bit camera can increase its dynamic range.

In the region before the AGC is triggered on, the relation between the average light intensity, I, of the hot fiber and the fusion current, i, can be approximated by:

$$I = A \exp[\alpha(i-i_0)2] \quad (1)$$

where the amplitude A is related to characteristics of the imaging system and the decline rate $\alpha$ and the initial current $i_0$ might be fiber-type related, respectively. The coefficients can be found by using curve fitting of Eq. (1) to the measured data. It is then found that the parameters $\alpha$ and A are fiber type independent for all seven fiber types. In the testing system used, the decline rate $\alpha=0.03$ and the amplitude A=18 are consistently valid. The initial current parameter $i_0$ is the only parameter which is dependent on the fiber type. The parameter values obtained from curve fitting of Eq. (1) to measured values are given in Table 1 for the seven fiber types.

TABLE 1

Measured parameters of Eq. (1) from 7 fiber types.

| Fiber type | $\alpha$ | A | $i_0$ (mA) |
|---|---|---|---|
| Single mode fiber (MCVD) | 0.03 | 18 | 6.2 |
| Single mode fiber (OVD) | 0.03 | 18 | 6.3 |
| Dispersion shifted (MCVD) | 0.03 | 18 | 5.7 |
| Dispersion shifted (OVD) | 0.03 | 18 | 6.4 |
| Titanium coated fiber | 0.03 | 18 | 4.3 |
| Multi-mode fiber | 0.03 | 18 | 4.5 |
| Silica core fiber | 0.03 | 18 | 7.1 |

Figure 3:
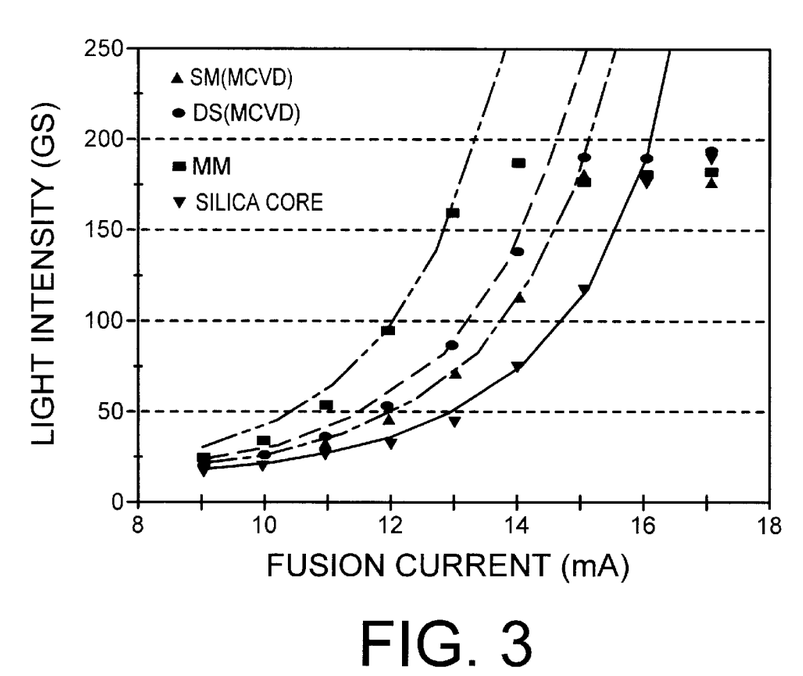
FIG. 3 is a diagram illustrating the light intensity as a function of the fusion current for different fiber types both as measured and calculated.
Figure 4:
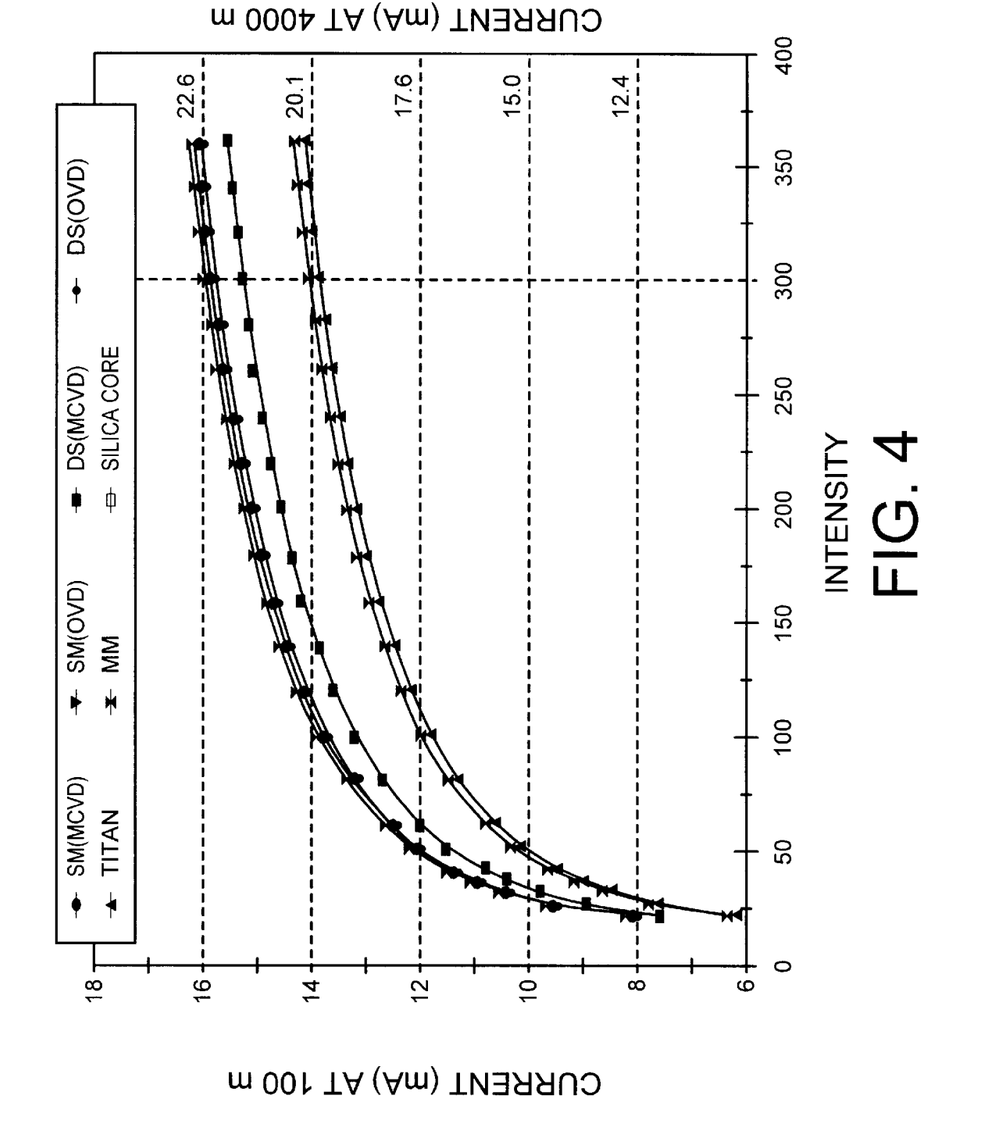
FIG. 4 is a diagram illustrating calculated fusion current values as a function of the luminescence intensity from the fiber ends.

A comparison between curves (1) calculated from the curve fitted parameters and the actual measured values of four fiber types is shown in the diagram of FIG. 3 where the light intensities are plotted as functions of the fusion currents used, the different marks denoting measured values and the graphs showing calculated curves. Good agreement can be observed before the AGC is active (i.e. in the case where the light intensity is lower than 160 grey scale units in the system used). The calculated relations between the fusion current and the average light intensity of the seven fiber types of Table 1 are illustrated in the diagram of FIG. 4. Optimal fusion currents are achieved when the light intensity reaches a threshold shown by the vertical dotted line for all the fiber types used.

For the calculated relations as illustrated in FIG. 4, we can observe that the optimal fusion currents (about 16 mA, 15.5 mA, 13.5 mA, and 16.5 mA for OVD, MCVD, multimode fiber, and silica core fiber types, respectively) are obtained for almost the same light intensity $I_{th}$ of about 300 grey scale units. This phenomenon indicates that a preset light intensity threshold can be employed to determine the optimal current for all fiber types at any altitude. However, the threshold might not be physically feasible because of the limited dynamic range of the camera.

Thus, for every splice, the current can start from a rather low value (say 10 mA) and then increase step by step. Meanwhile, the light intensity of the fiber end can be measured in real time. Whenever the intensity reaches the preset threshold, the current will be locked until the end of splicing.

However, in practice the fusion time is often not allowed to be so long as is required for waiting that such a fusion current ramp using a plurality of measurements is run. And also very often, when the current has arisen to a high level and part of the fiber is rather bright, the automatic gain control (AGC) will be triggered on and the relation of Eq. (1) will be ruined. Thus, a method which uses only a few steps of fusion current at a lower fiber brightness to determine the correct final fusion current is required and will be described hereinafter.

2. Fusion Current Calculation

From Table 1 we observe that the decline rate $\alpha$ and the amplitude A are constants for all fiber types. If the values of these two parameters are known in advance, there is only one unknown parameter, the start current $i_0$. Then it would be sufficient to make only one measurement of the light intensity for a suitably chosen current and then the light intensity function of Eq. (1) would be completely known and the optimal fusion current could be determined by finding the current i that according to the calculated relation (1) gives the light intensity value $I_{th}$. Making at least three measurements for different values of the fusion current would make a determination of all parameters $\alpha$, A and $i_0$ possible.

However, the amplitude A is obviously directly related to the set-up of the optical system, e.g. of the brightness adjustment thereof and could easily vary if some adjustment was made between different measurements or splices. Therefor the constantness of the amplitude cannot always be ensured. However, the amplitude A can be taken not to vary for the procedure comprising first measuring light intensity for some current values and then setting the fusion current accordingly for making a splice. Thus, there will always be necessary to determine two parameters, the amplitude and start current, the value of the decline rate being considered to be previously known, and thus at least two measurements must be made.

Thus two measurements are made for two different currents $i_1$ and $i_2$, where $i_1 < i_2$. The two corresponding intensities $I_1$ and $I_2$ are then, as given by Eq. (1):

$$I_1 = A \exp[\alpha(i_1 - i_0)^2] \quad (2)$$

and $$I_2 = A \exp[\alpha(i_2 - i_0)^2] \quad (3)$$

From (2) over (3), we obtain $$i_0 = i_0 = \frac{i_1 + i_2}{2} + \frac{1}{2\alpha(i_1 - i_2)} \ln \frac{I_1}{I_2} \quad (4)$$

And from (2), we have $$A = I_1 \exp[-\alpha a(i_1 - i_0)^2] \quad (5)$$

Thus, for a given theoretic intensity threshold $I_{th}$, which might not be physically feasible because of the AGC or the dynamic range of the CCD camera used, we should be able to obtain a corresponding current i from the knowledge of $i_1$, $i_2$, $I_1$, and $I_2$.

$$i = i_0 + \sqrt{\frac{1}{\alpha} \ln \frac{I_{th}}{A}} \quad (6)$$

Inserting (4) and (5) in (6), we have $$i = \frac{i_1 + i_2}{2} + \frac{1}{2\alpha(i_2 - i_1)} \ln \frac{I_1}{I_2} + \sqrt{\frac{1}{\alpha} \ln \frac{I_{th}}{I_1} + \left(\frac{i_1 - i_2}{2\alpha(i_2 - i_1)} \ln \frac{I_1}{I_2}\right)^2} \quad (7)$$

If we have $i_1 + 1 = i_2$, i.e. that the higher current intensity $I_2$ is 1 mA larger than the lower current intensity $I_1$, then Eq. (7) will degenerate to $$i = i_0 + \sqrt{\frac{1}{\alpha} \ln \frac{I_{th}}{I_1} + (i_1 - i_0)^2} \quad (8)$$

where $$i_0 = \frac{1}{2} + i_1 + \frac{1}{2\alpha} \ln \frac{I_1}{I_2} \quad (9)$$

Using Eq. (8), we can calculate a desired fusion current i from a preset intensity threshold $I_{th}$ by measuring the light intensity $I_1$ at the current intensity $i_1$, and the light intensity $I_2$ for the current $i_2 = i_1 + 1$, where $i_1$ and $i_2$ are chosen to be both located in a suitable working range. Of course other values than the step of 1 mA can between the currents can be used and in that case the general Eq. (7) is used.

3. Intelligent Fusion Current Selection

Using Eq. (8) or possibly Eg. (7) an intelligent fusion current selection can easily be implemented in a conventional, automatic fiber fusion splicer. The method has been tested in such a fusion splicer and very stable and encouraging results were obtained even for different test (start) currents as listed in Table 2. Seven different fiber types, the same as in Table 1, were used for a number of splices. For each fiber type, an optimized fusion current was found with a standard deviation less than 0.5 mA for different start currents.

Table 2. Fusion currents automatically selected by a conventional splicer for seven different fiber types at different starting currents $i_t$. The letters "NA" mean that the measured is not applicable for the cases, i.e. they are used in the cases where either $I_1 < I_{min}$ or $I_2 > I_{max}$. The parameters used to obtain the results are: $I_{th} = 300$ grey scale units, $I_{min} = 15$ grey scale units and $I_{max} = 170$ grey scale units.

| $i_t$ (mA) | 9 | 10 | 11 | 12 | 13 | 14 | mean | STD |
|---|---|---|---|---|---|---|---|---|
| SM (MCVD) | 16.69 | 16.24 | 15.81 | 15.74 | 15.78 | NA | 16.05 | 0.37 |
| SM (OVD) | 16.70 | 16.29 | 15.74 | 16.25 | 15.84 | 16.23 | 16.17 | 0.32 |
| DS (MCVD) | 16.16 | 15.19 | 15.39 | 15.20 | 15.41 | NA | 15.47 | 0.36 |
| DS (OVD) | 16.43 | 15.32 | 16.10 | 16.19 | 15.88 | 16.75 | 16.11 | 0.45 |
| Titanium | 13.92 | 13.96 | 13.45 | NA | NA | NA | 13.78 | 0.23 |
| MM | 14.43 | 14.16 | 13.72 | 14.08 | NA | NA | 14.09 | 0.25 |
| Silica core | 17.13 | 16.86 | 17.34 | 16.99 | 16.30 | 16.78 | 16.90 | 0.32 |

Figure 5:
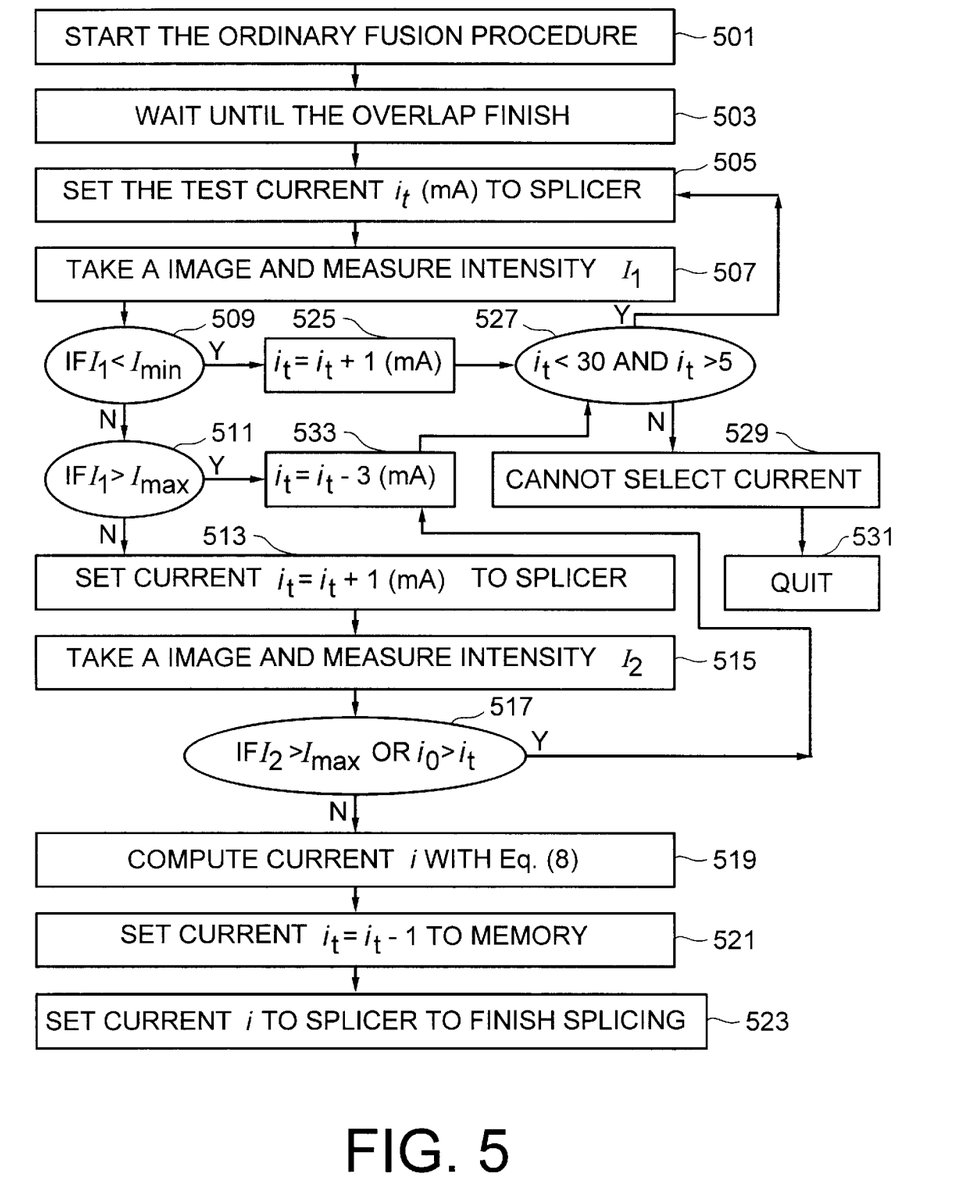
FIG. 5 is a flow chart of a procedure for automatic fusion current selection.

Using Eqs. (8) and (9), an intelligent fusion current selection can easily be implemented in a fiber fusion splicer of automatic type. A flow diagram of the procedure is shown in FIG. 5.

The procedure starts in a block 501, in which the ordinary fusion procedure is initiated. In this step the necessary rough alignment of the fiber end is made and in the next block 503 it is awaited, until the fiber end surfaces have been moved close to each other. Then in the block 505 the test current $i_t$ corresponding to $i_1$ above is chosen in some suitable way, for example to a rather high value with some reasonable interval. If there is some value already stored, it can be used. Then in a block 507 an image is taken and is analyzed to find the intensity $I_1$, for example as suggested above it can taken to be the average light intensity along a line perpendicular to a fibre end, the line segment being located centrally with respect to the fibre longitudinal axis and symmetrically thereto, e.g. encompassing half the fiber width. In a next block 509 it is determined whether the measured intensity $I_1$ is smaller than a minimum light intensity value $I_{min}$. The minimum value $I_{min}$ is chosen to be the smallest value for which an acceptable measurement can be made and is thus chosen to be well located above the noise level of the measuring system. If the decision of the block 509 is that the measured and analyzed light intensity is good for the measurement purpose, i.e. not smaller than the minimum light intensity $I_{min}$, a block 511 is executed. There the measured and analyzed light intensity $I_1$ is compared to a maximum light intensity value $I_{max}$. The maximum light intensity value $I_{max}$ is selected, that for light intensity values equal to or larger than it probably the AGC function of the camera would be activated and distort the measurements. If it is found in the block 511 that the measured light intensity $I_1$ is not larger than the maximum light intensity value $I_{max}$ a block 513 is executed and there the test current value $i_t$ corresponding to $i_2$ to be used for the next measurement is determined and set to the previously used test current intensity value $i_1$ increased by a fixed, predetermined current intensity increment of e.g. 1 mA, as suggested above, i.e. $i_t=i_t+1$ (mA). Then a new image is taken in a block 515 for the test current $i_t$ ($=i_2$) and a second measured and analyzed intensity $I_2$ is determined from the captured picture. In a block 517 it is then first determined whether the second measured intensity value $I_2$ is larger than the maximum light intensity value $I_{max}$. In the block 517 also the start current $i_0$ is calculated according to Eq. (9) using the previously determined, stored value of the decline rate $\alpha$ and it is determined whether the calculated start current value $i_0$ is larger than the first or previously used test current value $i_1$. If the two determinations in this block 517 give the answer no, the test currents used ($i_1$ and $i_2$) are suitable for determining an optimal fusion current. Thus the fusion current i is calculated according to Eq. (8) in a block 519 using a stored value of the decline rate $\alpha$. The first used test current value $i_1$ is then stored in the processor memory in the block 521 for a possible future use for another splice. Finally, in a block 523 the determined fusion current i is used in the splicer for making the actual splice between the two fiber ends.

If it was determined in the block 509, that the first measured intensity $i_1$ was smaller than the minimum light intensity value $I_{min}$ a block 525 is executed. A new first test current value is here obtained by incrementing the first used test current value by some suitable increment, e.g. 1 mA, in order to obtain a greater light intensity in the captured image. Then in a block 527 the new first test current value $i_t$ ($=i_1$) is checked to have a value within a valid interval, e.g. as suggested between the values of 5 mA and 30 mA. If the new first test current value is located within this range the block 505 is again executed for the new first current value. If the new current value is outside said range, obviously a valid test current cannot be selected as is announced or displayed in a suitable way in a block 529 and then the procedure is ended in a block 531.

If it was decided in the block 511 that the first measured and analyzed light intensity value $I_1$ was larger than the maximum light intensity value $I_{max}$, above which the AGC can distort the measurements, a block 533 is executed. Obviously the light intensity is too high and the test fusion current must be reduced and this is made by decrementing the first used test current by a suitable increment, e.g. as suggested comprising 3 mA, i.e. a new test current $i_t$ is obtained from $i_t=i_t-3$ (mA). After the block 533 the new test first current value is tested whether it is within the valid range and the procedure thus proceeds to the block 527, as described above, in which a decision is made and after which the procedure continues in the way as already described.

If it was determined in the block 517 that either one of the conditions in this decision block was fulfilled, i.e. that the second measured light intensity value $I_2$ was larger than the maximum light intensity $I_{max}$ or the start current $i_0$ is larger than the second test current value $i_2$, the latter condition signifying that the measurements were made on a wrong portion of the exponential curve of Eq. (1), obviously the used test currents have been too high and therefore must be reduced. Therefore the block 533 comprising a reduction of the second test current by a predetermined suitable amount is executed in the same manner as has been described above. After the block 533 the procedure continues to the block 527 as above.

The method described above is advantageously performed by an automatic image processing and positioning device used for splicing optical fibers, the components of which are schematically illustrated in FIG. 6.

In the schematic picture of FIG. 6 a fiber splicing device of the automatic type is shown having retainers 9, in which the fiber ends are placed and are retained during the positioning and the splicing. The retainers 9 are movable in three orthogonal coordinate directions both in parallel to the longitudinal direction of the fibers and in two directions perpendicular to this direction which then also are perpendicular to the illuminating directions of light emitted from the light sources 11. The retainers 9 are operated along suitable mechanical guides, not shown, by control motors 13. Electric conducting lines to the electrodes 7, the motors 13 and the lamps 11 are provided from an electronic circuit module 15 and in particular from driver circuits 17, 19 and 21 respectively arranged therein. From the TV camera 7 an electric line is arranged to a video interface 23 in the electronic circuit module 15, from which a suitable image signal is delivered to an image processing and image analysis unit 25 producing among other things pictures which can be displayed on a monitor 26. The various procedural steps for welding the fibers 1 to each other are controlled by logic circuits 27, e.g. in the shape of a suitable microprocessor. The logic circuits 27 comprises submodules for executing the procedural steps as described above for determining an optimal fusion current and for splicing the fibers 1 using this current. It thus comprises a general control submodule 29 for controlling the displacement of the fiber 1 ends in relation to each other by an activation of the motors 13 in suitable displacement directions, provides a signal to the image processing and image analysis unit 25 for starting an analysis of an obtained picture and a determination of the light intensity. Further, the control circuit 29 controls the activation of the light sources 11 by sending suitable signals to the driver circuit 21 thereof and the application of a high electric voltage to the electrodes 43 and the time period during the electric voltage is to be delivered and then setting the electric current between the electrodes to the various required values, by providing appropriate signals to the driver circuit 17. Further, a memory 31 is used for storing previously determined parameters, such as the decline rate $\alpha$, and values for previously used test currents. Calculation circuits 33 perform the calculation of the required parameters, such as calculation the function values of Eqs. (8) and (9), and can then use parameters previously stored in the memory 31. Finally, determination circuits 35 are provided for determining the current intensity which gives the threshold light intensity value $I_{th}$.

Additional advantages and modifications will readily occur to those skilled in the art. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents.

What is claimed is:

1. A method of determining a fusion current to be made to pass between electrodes for welding ends of two optical fibers to each other, the method comprising the steps of:

placing the ends between the electrodes;

making different currents pass between the electrodes, which currents are significantly lower than a range, in which the fusion current can be expected to be located, whereby the ends are heated;

measuring intensity of light emitted from the ends when the ends are heated using the different currents;

obtaining a functional relationship from the relation of measured values of the intensity of light and the different currents;

extrapolating the functional relationship to find an extrapolated value of a current intensity which will produce a value of intensity of light equal to a predetermined, desired light intensity value; and taking the extrapolated value as the fusion current.

2. The method of claim 1, comprising the additional step of:

taking as a template of the functional relationship an exponential function of a squared difference of a test current i and a start current value $i_0$.

3. The method of claim 2, wherein the exponential function is $$I = A \exp[\alpha(i-i_0)2]$$

where I is a value of intensity of light and A, $\alpha$ and $i_0$ are parameters.

4. A method of determining a fusion current to be used for splicing ends of two optical fibers to each other, the splicing being made by means of an electric arc formed between electrodes for heating the ends, the current passing between the electrodes during the splicing being the fusion current, the method comprising the steps of:

placing the ends with end surfaces thereof adjacent each other between the electrodes;

measuring intensity of light emitted from the ends when a first number of different test currents is made to pass between the electrodes for heating the ends to lower temperatures than a temperature at which the ends are spliced to each other;

calculating from measured values of intensity of light values of a second number of parameters for a predetermined general function describing the dependence of the intensity of light on the test currents and using in the calculation previously determined values of parameters; and determining from the predetermined function using the values of the second number of parameters and the previously determined values of parameters used in the calculation a value of a test current which gives an intensity of light equal to a predetermined value and taking this value as a value of the fusion current.

5. The method of claim 4, comprising the additional step of:

taking as a template of the predetermined general function an exponential function of a squared difference of a test current i and a start current value $i_0$.

6. The method of claim 5, wherein the exponential function is $$I = A \exp[\alpha(i-i_0)2]$$

where I is a value of intensity of light and A, $\alpha$ and $i_0$ are parameters.

7. A method of determining a fusion current to be used in splicing ends of two first optical fibers to each other by means of an electric arc formed between electrodes for heating the ends of the two first optical fibers, the current passing between the electrodes during the splicing being a fusion current, the method comprising the steps of:

placing the ends of the two first optical fibers with end surfaces thereof adjacent each other between the electrodes;

measuring intensity of light emitted from the ends of the two first optical fibers when a first number of different test currents is made to pass between the electrodes for heating the ends of the two first optical fibers to lower temperatures than a temperature at which the two first optical fibers are fusioned to each other;

calculating from measured values of the intensity of light values of a second number of parameters for a predetermined function describing the dependence of the intensity of light on the test currents; and determining from the predetermined function using the values of the second number of parameters a value of a test current which gives an intensity of light equal to a predetermined value and taking this value as a value of the fusion current.

8. The method of claim 7, comprising the additional steps of:

placing ends of two second optical fibers with end surfaces thereof adjacent each other between the electrodes;

measuring intensity of light emitted from the ends of the two second optical fibers when a third number of test currents, which are different from each other, are made to pass between the electrodes for heating the ends of the two second optical fibers to lower temperatures than a temperature at which the two second optical fibers are fusioned to each other, the third number being lower than the first number;

calculating from measured values of the intensity of light values of a fourth number of parameters for the predetermined function, the fourth number being lower than the second number, the values of parameters for which values are then not calculated being taken to be equal to the values of corresponding parameters among the second number of parameters; and determining from the predetermined function using the values of the fourth number of calculated parameters and values of appropriate parameters among the second number of parameters a value of a test current which gives an intensity of light equal to a predetermined value and taking this value as a value of the fusion current for the two second optical fibers.

9. The method of claim 8, wherein the two second optical fibers are the same kind as the two first optical fibers.

10. The method of claim 8, wherein the first number is larger than two and the third number equals two.

11. The method of claim 7, comprising the additional step of:

taking as a template of the predetermined function an exponential function of a squared difference of a test current i and a start current value $i_0$.

12. The method of claim 11, wherein the exponential function is $$I = A \exp[\alpha(i-i_0)2]$$

where I is a value of intensity of light and A, $\alpha$ and $i_0$ are parameters.

13. The method as claimed in claim 1 also comprising splicing ends of two optical fibers to each other, wherein in the step of placing the ends between the electrodes end surfaces of the ends are placed at or in contact with each other, the method comprising the additional step of:

setting an intensity of current passing between the electrodes to the value of the fusion current as taken in any of claims 1–12 during a time period sufficient to fusion the ends of the two optical fibers to each other.

14. A device for determining a fusion current to be used in splicing ends of two optical fibers to each other by means of an electric arc, the device comprising electrodes for forming an electric arc between the electrodes;

driver circuits connected to the electrodes for applying a high voltage between the electrodes and making a current pass between the electrodes; and retaining and positioning means for retaining ends of two optical fibers and for placing the ends at each other or in abutting relationship with each other between points of the electrodes and in the electric arc;

the device further comprising measuring means for measuring intensity of light emitted from the ends;

control means connected to the measuring means and the driver circuits, the control means being arranged, when a splice is to be made between ends of two optical fibers, to control the driver circuits to make different test currents pass between the electrodes for heating the ends to lower temperatures than a temperature at which the ends are fusioned to each other and to control the measuring means to measure intensity of light emitted for the test currents;

calculating and determining means connected to the measuring means and to the control means for extrapolating from values of intensity of light measured by the measuring means and values of intensity of the test currents an extrapolated current intensity value, for which the electrodes will produce a light intensity equal to a predetermined, desired light intensity value, and for transferring the extrapolated current intensity value to the control means to be used as a value of the fusion current.

15. The device of claim 14, wherein the calculating and determining means are arranged to make the extrapolating by using an exponential function of a squared difference of a test current i and a start current value $i_0$.

16. The device of claim 15, wherein the exponential function is $$I = A \, \exp[\alpha(i-i_0)2] \qquad (1)$$

where I is a value of intensity of light and A, $\alpha$ and $i_0$ are parameters.

17. A device for determining a fusion current to be used in splicing ends of two optical fibers to each other by means of an electric arc, the device comprising electrodes for forming an electric arc between the electrodes;

driver circuits connected to the electrodes for applying a high voltage between the electrodes and for making a current pass between the electrodes;

retaining and positioning means for retaining ends of two optical fibers and for placing the ends at each other or in abutting relationship with each other between points of the electrodes and in the electric arc;

the device further comprising measuring means for measuring intensity of light emitted from the ends;

control means connected to the measuring means and the driver circuits, the control means being arranged, when a splice is to be made between two optical fibers, to control the driver circuits to make different test currents pass between the electrodes for heating ends of the two optical fibers to lower temperatures than a temperature at which the ends of the two optical fibers are fusioned to each other and to control the measuring means to measure intensity of light emitted for the test currents;

memory means connected to the control means;

calculating means connected to the measuring means, the control means and the memory means for calculating from values of intensity of light measured by the measuring means and values of intensity of the test currents parameters of a predetermined general function describing dependence of the intensity of light on the test currents and by using other parameters previously stored in the memory means; and determining means connected to the calculating means for determining from the predetermined general function using the parameters calculated by the calculating means a value of a test current which gives an intensity of light equal to a predetermined value and for taking this value as a value of the fusion current.

18. The device of claim 17, wherein the calculating means are arranged to use as the predetermined general function an exponential function of a squared difference of a test current i and a start current value $i_0$.

19. The device of claim 18, wherein the exponential function is $$I = A \, \exp[\alpha(i-i_0)2] \qquad (1)$$

where I is a value of intensity of light and A, $\alpha$ and $i_0$ are parameters.

20. A device for determining a fusion current for splicing ends of two optical fibers to each other by means of an electric arc, the device comprising electrodes for forming an electric arc between the electrodes;

driver circuits connected to the electrodes for applying a high voltage between the electrodes and making a current pass between the electrodes;

retaining and positioning means for retaining ends of two optical fibers and for placing the fiber ends at each other or in abutting relationship with each other between points of the electrodes and in the electric arc;

the device further comprising measuring means for measuring intensity of light emitted from the ends;

control means connected to the measuring means and the driver circuits, the control means being arranged, when a splice is to be made between ends of two optical fibers, to control the driver circuits to make a first number of different test currents pass between the electrodes for heating the ends to lower temperatures than a temperature at which the ends are fusioned to each other and to control the measuring means to measure intensity of light emitted for the test currents;

calculating means connected to the control means and the measuring means for calculating from values of intensity of light measured by the measuring means and values of intensity of the test currents a second number of parameters for a predetermined function describing dependence of intensity of light on the test currents; and determining means connected to the calculating means for determining from the predetermined function using the second number of the parameters calculated by the calculating means a value of a test current which gives an intensity of light equal to a predetermined value and taking this value as a value of the fusion current.

21. The device of claim 20, further comprising memory means for storing at least one of the second number of the parameters, the memory means being connected to the control means and the calculating means;

the control means being arranged when a splice between ends of two optical fibers is to be made, in the case where the memory means hold parameters calculated during a previous measurement, to control the driver circuits to make a third number of test currents, which are different from each other, to pass between the electrodes for heating the ends to lower temperatures than a temperature at which the fibers are fusioned to each other, the third number being lower than the first number, and to control the measuring means to measure intensity of light emitted from the ends for the third number of test currents;

the calculating means being arranged to calculate from measured values of intensity of light a fourth number of parameters for the predetermined function, the fourth number being lower than the second number, and to retrieve from the memory means parameters which are not calculated and to use them in the calculation;

the determining means being arranged to determine from the predetermined function using the fourth number of parameters and retrieved parameters a value of a test current which gives an intensity of light equal to a predetermined value and to take this value as a value of the fusion current for the ends of the two optical fibers to be spliced.

22. The device of claim 20, wherein the calculating means are arranged to use as the predetermined function an exponential function of a squared difference of a test current i and a start current value $i_0$.

23. The device of claim 19, wherein the exponential function is $$I=A\ \exp[\alpha(i-i_0)2] \tag{1}$$

where I is a value of intensity of light and A, $\alpha$ and $i_0$ are parameters.

24. The device of claim 21, wherein the first number is larger than two and the third number equals two.

25. The device as claimed in claim 14 also arranged for splicing ends of two optical fibers to each other, wherein the retaining and positioning means are arranged to place the ends substantially in contact with each other; and the control means are arranged to control the driver circuits for making a current pass between the electrodes, the current having an intensity equal to a value of the fusion current, and making this current pass during a sufficiently long time period to fusion the ends of the two optical fibers to each other.

* * * * *